(12) United States Patent
Chang et al.

(10) Patent No.: US 6,238,625 B1
(45) Date of Patent: May 29, 2001

(54) SEALED HIGH-DENSITY ON-LINE MEASURING DEVICE

(75) Inventors: Yong Keun Chang, Taejon; Jong Dae Lee, Seoul; Yong Ho Jung, Cheollabuk-Do, all of (KR)

(73) Assignee: Korea Advanced Institute of Science and Technology (KR)

( * ) Notice: Subject to any disclaimer, the term of this patent is extended or adjusted under 35 U.S.C. 154(b) by 0 days.

(21) Appl. No.: 09/216,156

(22) Filed: Dec. 18, 1998

(30) Foreign Application Priority Data

Dec. 20, 1997 (KR) .................................................. 97-71325

(51) Int. Cl.[7] .................................................. G01N 21/05
(52) U.S. Cl. ...................... 422/82.09; 436/165; 356/440; 356/246
(58) Field of Search .................................... 422/62, 82.05, 422/82.09; 436/165; 356/319, 323, 326, 413, 246, 440

(56) References Cited

U.S. PATENT DOCUMENTS

| | | | |
|---|---|---|---|
| 2,490,345 | * 12/1949 | Flatford et al. | |
| 3,614,243 | * 10/1971 | Harvey | 356/246 |
| 3,714,445 | * 1/1973 | Blachere et al. | 250/218 |
| 3,740,156 | * 6/1973 | Heigl et al. | 356/95 |
| 5,139,333 | * 8/1992 | Reinhard | 356/246 |
| 5,268,736 | * 12/1993 | Prather | 356/246 |
| 5,371,020 | * 12/1994 | Frischauf | 436/165 |
| 5,510,621 | * 4/1996 | Goldman | 250/343 |
| 5,905,271 | * 5/1999 | Wynn | 250/573 |

* cited by examiner

Primary Examiner—Jeffrey Snay

(57) ABSTRACT

The present invention relates to a sealed high-density on-line measuring device for spectrophotometer whose cuvette holder is linked to a reactor, which comprises a base; a fixed plate for light passage, which is vertically placed on the base; a moving plate for light radiation, which is vertically placed on the base at an opposite side to the fixed plate so that it can slide on the base horizontally; inlet and outlet for sample passage, each of which is positioned at outer side of the moving plate; a metal ring linking the fixed plate and the moving plate; and, upper and lower shielders each of whose ends is in contact with the fixed plate and moving plate, respectively, to give a sealed space. In accordance with the sealed on-line measuring device of the invention, high concentrations of samples in solutions can be measured without dilution, by way of employing a newly designed cuvette holder in a spectrophotometer fitted to a reactor.

9 Claims, 12 Drawing Sheets

SEALED HIGH-DENSITY ON-LINE MEASURING DEVICE

FIELD OF THE INVENTION

The present invention relates to a sealed high-density on-line measuring device by which high concentrations of samples in solutions can be measured, more specifically, to a sealed high-density on-line measuring device which can measure high concentrations of the solid materials or dissolved substances without dilution by the absorbance of the samples by way of regulating path length of the radiated light in the solutions.

BACKGROUND OF THE INVENTION

In general, methods for measuring the concentration of materials in solutions are classified into off-line method and on-line method, according to the nature of measurement or measuring device.

In the measurement of cell concectration during a fermentation process, the off-line method includes a dry weight measurement and an absorbance measurement where a spectrophotometer is employed to determine the absorbance of diluted medium. In the latter method, dilution is inevitable since the linearity between the absorbance and cell concentration is rather limited, grounded on the usage of a conventional quartz-made 1 cm cuvette or a test tube of 1 cm diameter, which, in turn, restricts the available measurement range to a very low concentration. To overcome this limitation of narrow measuring range, a device which can measure high concentration by regulating light path length has been suggested in the art (see: Fugita, T., Nunomura, K., Appl. Microbiol., 16(2):212–216(1968)). However, the device has been proven to be rather limited to measuring of microorganism by off-line method. The off-line method has further shortcomings as follows: when sampling is carried out in a fermenter, the fermenter may be contaiminated with saprophytes; errors may be generated in frequent handling and dilution of the sample; and, real-time assay is impossible. Therefore, many concerns and works are devoted to the on-line measurement which does not need to flow out the culture from a fermentor like sampling or dilution.

In one-line measurement, since there is no outflow of sample, measuring of the dissolved substances and solid materials in a reactor under a chemical or biological process can be performed to guarantee easy control and suitable operation. Until now, as one of the on-line measuring devices without outflow and dilution of the reactants, an electrode equipped measuring device fitted to a reactor has been proposed in the art. However, this device has also revealed some drawbacks of expensiveness, instability, and errors caused by the reactor condition.

Therefore, there are strong reasons for developing a novel on-line measuring device with stability and accuracy which can simply determine the concentrations of dissolved substances, solid materials, and products in many biological or chemical processes.

SUMMARY OF THE INVENTION

In accordance with the present invention, the inventors fabricated an on-line measuring device which can measure high concentrations of samples in solutions without dilution, by way of employing a newly designed cuvette holder in a spectrophotometer fitted to a reactor, where path lengths of the radiated light in the solution is finely regulated.

A primary object of the present invention is, therefore, to provide a novel on-line measuring device which can measure high concentrations of samples by regulating the light path length.

BRIEF DESCRIPTION OF THE DRAWINGS

The above and the other objects and features of the present invention will become apparent from the following description given in conjunction with the accompanying drawings, in which.

DETAILED DESCRIPTION OF THE INVENTION

Figure 1:
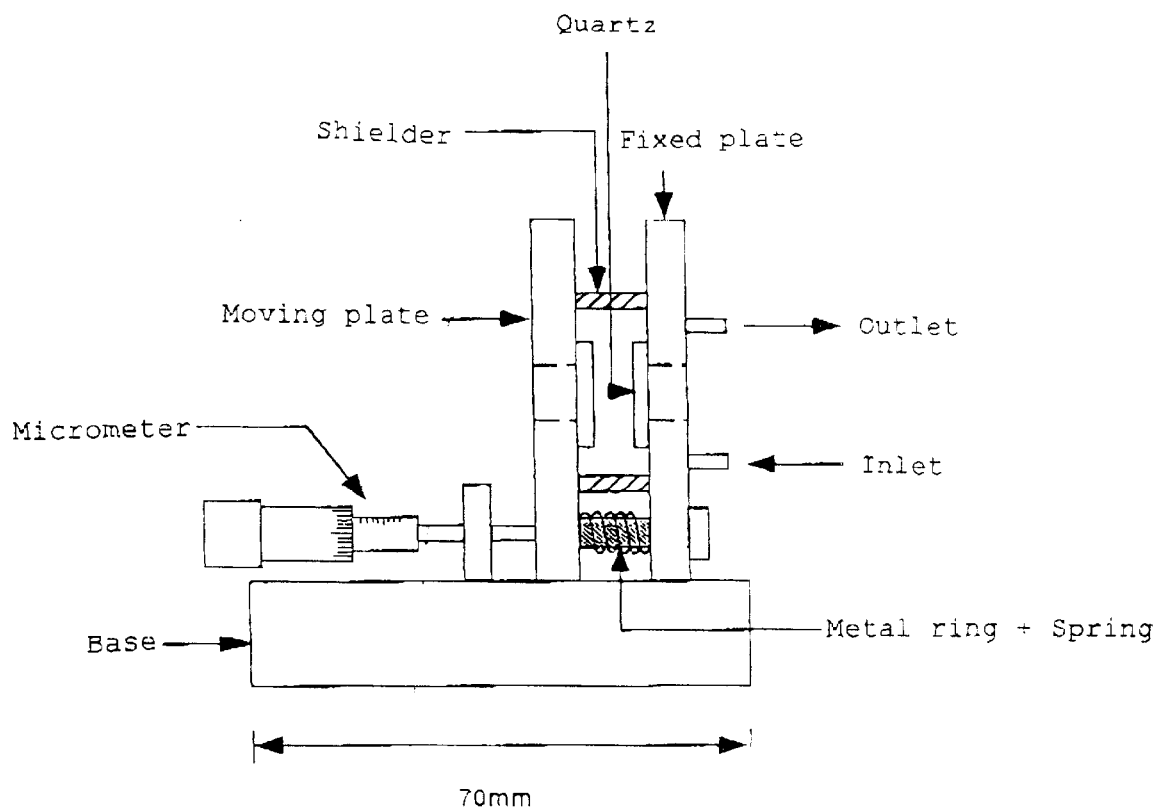
FIG. 1 is a schematic diagram showing a sealed high-density on-line measuring device of the present invention.

Referring to FIG. 1, there is provided the structure of a sealed high-density on-line measuring device of the present invention. The sealed high-density on-line measuring device for spectrophotometer has a cuvette holder which is linked to a reactor, which comprises:

a base;

a fixed plate for light passage, which is vertically placed on the base;

a moving plate for light radiation, which is vertically placed on the base at an opposite side to the fixed plate so that it can slide on the base horizontally;

inlet and outlet for sample passage, each of which is positioned at outer side of the moving plate;

a metal ring linking the fixed plate and the moving plate; and upper and lower shielders each of whose ends is in contact with the fixed plate and moving plate, respectively, to give a sealed space.

In fabricating a sealed high-density on-line measuring device which is able to regulate light path length of the invention, duralumin which has an excellent nature of endurance and anticorrosion is preferably used. Path length of the radiated light is regulted by fine control of a distance between the fixed plate and the moving plate, and can be more finely controlled by employing a micrometer. Fixed plate and moving plate are linked by a sliding bearing of the metal ring, which conveys minor rotation of the micrometer to the moving plate. In addition, a round-shaped hole with quartz glass plate of 1/16 inch width, is provided at the same position of each of the fixed plate and the moving plate to pass a radiated light through them, and a transparent plate may be attached on the sealed space-faced side of two plates. To ease the control of the light path length, one set of shielders, i.e., upper and lower shielders made of pleated flexible material or elastic material, preferably, metal rings (e.g., stainless steel ring) covered with rubber, are fixed to the moving plate and fixed plate to give a sealed space. In addition, for the continuous circulation of samples, inlet and outlet are positioned at outer side of the fixed plate. On the other hand, the moving plate and the micrometer should be positioned to ensure smooth rotation of the micrometer. Accordingly, there may be brought about a clearance by which slight changes of the micrometer are not conveyed to the moving plate. To solve the clearance problem, a spring is provided on a metal ring positioned between the fixed and moving plates, by which minor rotation of the micrometer can be conveyed to the moving plates.

On-line measuring of concentration using the sealed measuring device of the invention is accomplished by passing a light of wavelength employed in conventional spectrophotometers or a laser beam through a hole of the fixed and moving plates while circulating the samples through inlet and cutlet of the fixed plates.

The present invention is further illustrated in the following examples, which should not be taken to limit the scope of the invention.

EXAMPLE 1

Determination of the absorbance of yeast culture

A yeast isolate stored in agar plate was inoculated in 100 ml of YPD culture medium of Table 1 for seed culture and cultured for 12 hours in a 250 ml baffled flask. Then, 3 ml of the culture was inoculated in two flasks containing 200 ml of YPD culture medium and cultured for 20 hours in a shaking incubator maintained at 30° C. and 200 rpm.

TABLE 1

Composition of YPD culture medium (unit: g/L)

| Component | Content |
|---|---|
| Yeast extract | 10 |
| Peptone | 20 |
| Glucose | 20 |

400 ml of seed culture obtained in the above was inoculated in a 7-liter fermenter(Korea Fermenter Inc., Korea) containing 4 L of YPD culture medium, and batch culture was carried out at a temperature 30° C. while maintaining pH of 5.5 using 2N-HCl solution and diluted aqueous ammonia. The shaking speed and aeration rate were controlled at 200 rpm and 2 vvm, respectively(where, 1 vvm is the rate of aerating the same volume with the reactor volume per 1 min). To obtain a high level of cell concentration, the cell culture obtained in the batch fermentation was centrifuged at 8000 rpm for 10 min. Some part of supernatant was discarded, suspended to reach the cell concentration of over 100 g/L, and put in a fermenter under a sterilized condition. While circulating in a spectrophotometer fitted with a sealed high-density on-line measuring device of the invention, the cell concentration was determined as described below. On the other hand, for the direct measurement of cell concentration, 500 ml of culture medium was centrifuged, washed with 0.85% NaCl, dried in a 70° C. oven for 1 day, and the dry cell weight was measured.

Figure 2:
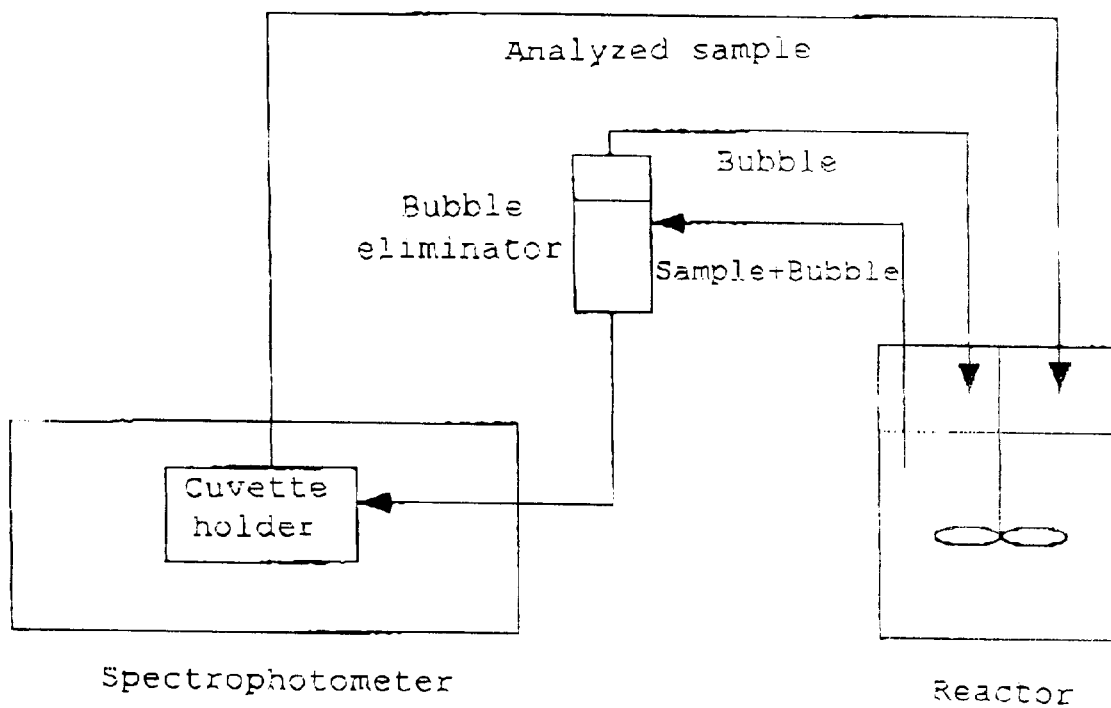
FIG. 2 is a schematic diagram showing the connections of a spectrophotometer, a reactor, and a bubble eliminator for the on-line measurement of cell concentrations by employing the sealed high-density on-line measuring device.

On-line measuring was carried out by using a sealed high-density on-line measuring device of the invention: First, a spectrophotometer(HP-8453, Hewlett-Packard, U.S.A.) was fitted with a sealed high-density on-line measuring device. As shown in FIG. 2, inlet and outlet of the device were connected to outlet of a bubble eliminator and to a reactor, respectively. Culture medium was circulated by a pump so that the culture medium in a fermenter can pass through the bubble eliminator, go through the sealed high density on-line measuring device, and finally be returned to the reactor. Then, the distance between moving plate and fixed plate was controlled appropriately using a micrometer, and the absorbance was measured by penetrating 600 nm of radiant light. Also, the absorbances of several cell concentrations obtained by a serial dilution were determined in a similar manner as described above.

Figure 3:
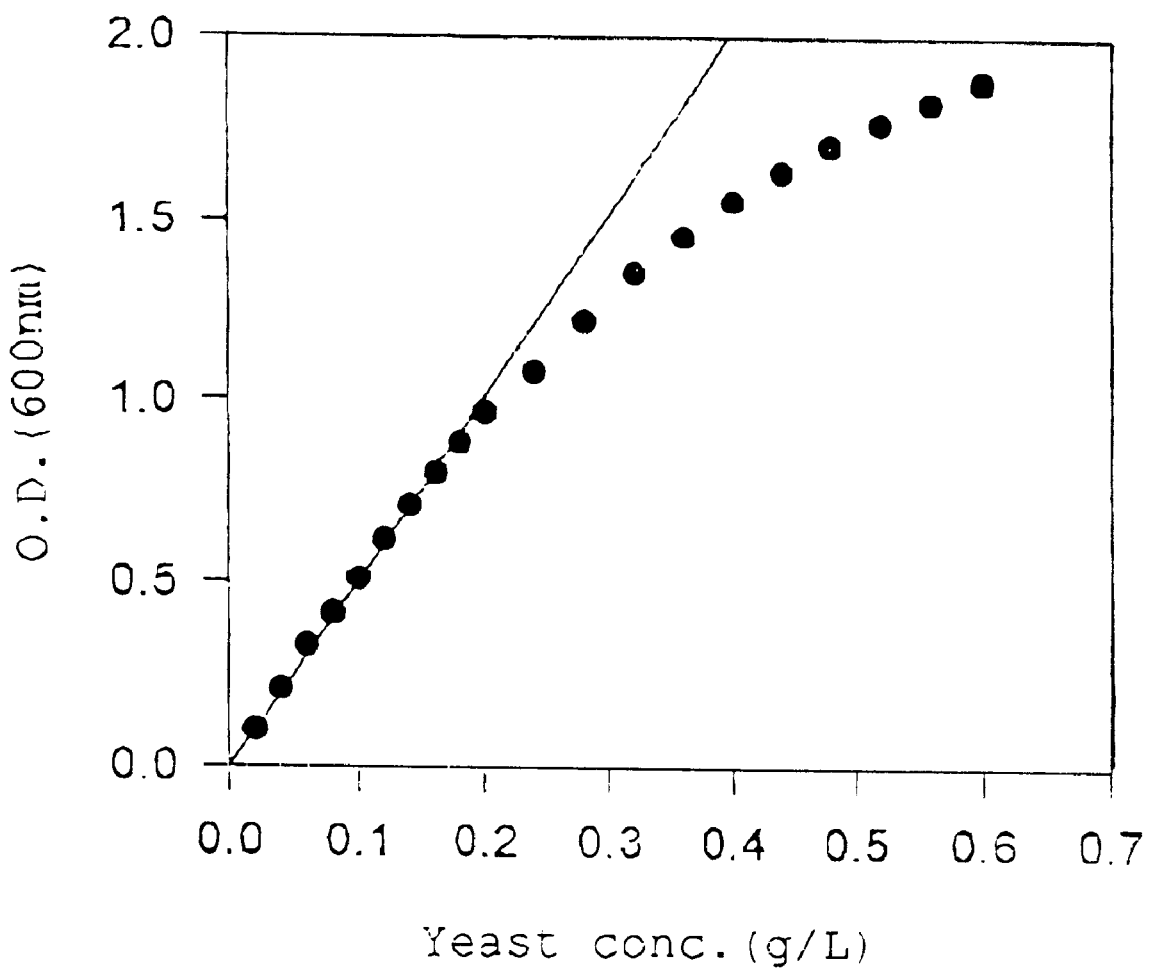
FIG. 3 is a graph showing the relationship between the absorbance measured with a 1 cm-cuvette used in conventional spectrophotometers and yeast concentration.

FIG. 3 shows the relationship between the absorbance measured by a spectrophotometer employing a conventional 1 cm-cuvette and yeast concentration. As shown in FIG. 3, linearity between the absorbance and cell concentration appeared in a range of low concentration, while curved parabola was obtained above 0.2 g/L.

Figure 4:
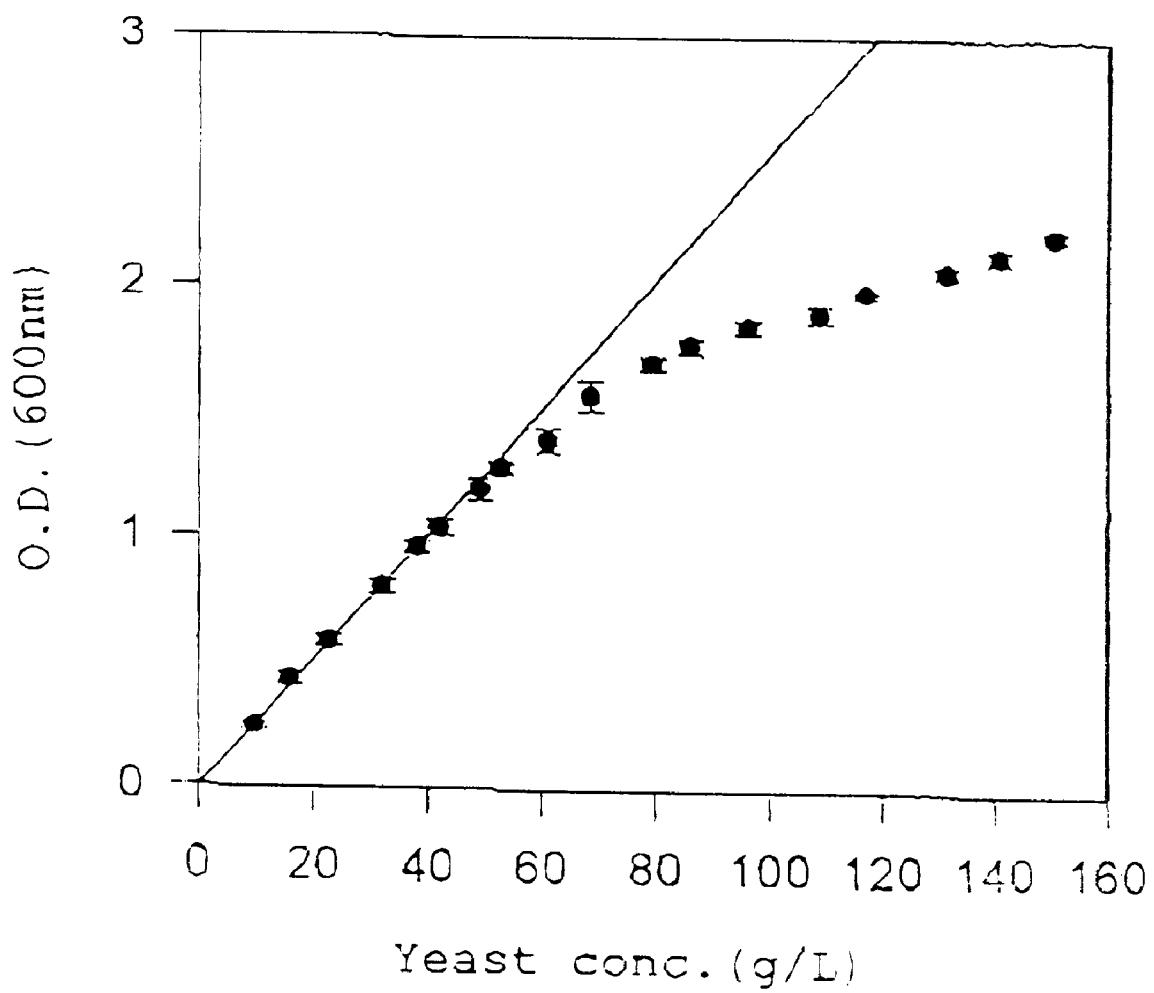
FIG. 4 is a graph showing the relationship between the absorbance measured by a spectrophotometer fitted with a sealed high-density on-line measuring device and yeast concentration.

FIG. 4 shows the relationship between yeast concentration and the absorbance measured by a sealed high-density on-line measuring device where effective path length of radiated light was 47 μm. As shown in FIG. 4, linearity appeared to a concentrated range of about 40 g/L and, above that concentration, the slope of the graph was quite deviated from the linearity. Comparing this result with those in FIG. 3, on-line measuring using the apparatus of the invention can extend the linearity-region by about 200 times than that of conventional method. The error range appeared in FIG. 4 is an average of 5 times of repeated experiments carried out for a constant cell concentration. The standard deviation was as low as 0.008–0.090 g/L in whole range of experiments, which makes sure the excellent reproducibility of measurement by the on-line measuring device in the invention. When the aeration rate was increased up to 4 vvm, the measured value was scarcely affected due to a perfect operation of the bubble eliminator fitted with the sealed high-density on-line measuring device.

Figure 5:
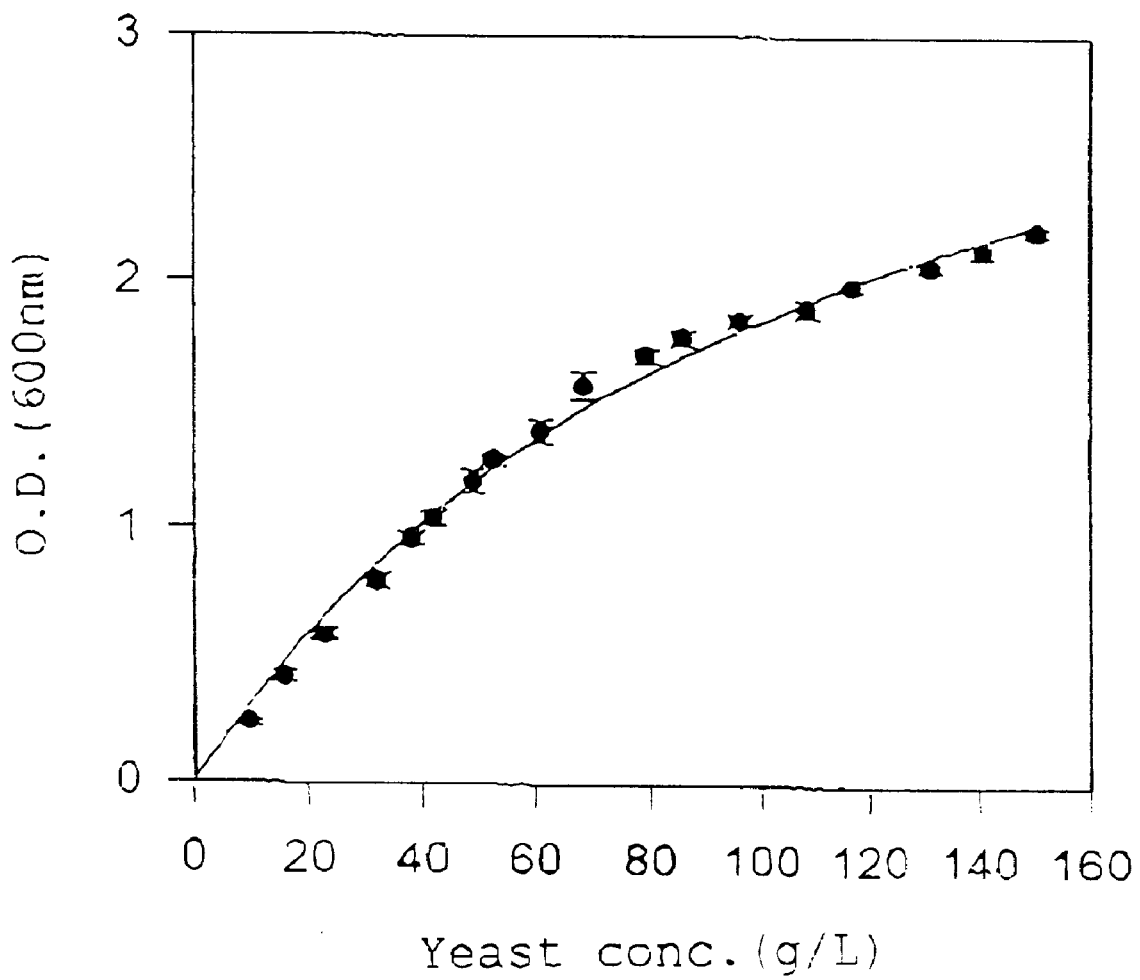
FIG. 5 is a graph showing the results of FIG. 4 which are calculated by a saturation-type equation.

FIG. 5 is a graph showing the results of FIG. 4, which are calculated by a saturation-type equation as below:

Cell concentration=(a×absorbance)/(b+absorbance)

wherein, a and b are constant (in case of yeast, a=111.32, b=3.9).

In case of employing a standard curve shown in FIG. 5, on-line measuring of yeast concentration as above 100 g/L can be realized without a significant error, by the sealed high-density on-line measuring device of the

EXAMPLE 2

Determination of the absorbance of cylindrical Lactobacillus culture medium

MRS (De Man-Rogosa-Sharpe) medium as shown in Table 2 below was used for the culture of Lactobacillus. The stored Lactobacillus isolate was inoculated in 250 ml baffled flask containing 100 ml of MRS medium, and the first seed culture was carried out for 12 hours in a shaking incubator under a condition of 40° C., 200 rpm. Then, 3 ml of the first seed culture was inoculated in two 500 ml flasks containing 200 ml of MRS midium, and cultured for 12 hrs under a condition of 40° C., 200 rpm. 400 ml of the second seed culture was used for the inoculation in a fermenter. The fermentation was carried out in a similar fashion as described in Example 1, except that the temperature is 40.5° C., pH condition 5.67, shaking speed 200 rpm and aeration rate 2 vvm.

TABLE 2

The composition of MRS medium

| Component | Content* |
| --- | --- |
| Glucose | 20 |
| Yeast extract | 5 |
| Beef extract | 10 |
| Potato peptone #3 | 10 |
| $CH_3COONa3H_2O$ | 5 |
| Ammonium citrate | 2 |
| $K_2HPO_4$ | 2 |
| $MgSO_47H_2O$ | 0.1 |
| $MsSO_47H_2O$ | 0.005 |
| Tween 80 | 1 |

Figure 6:
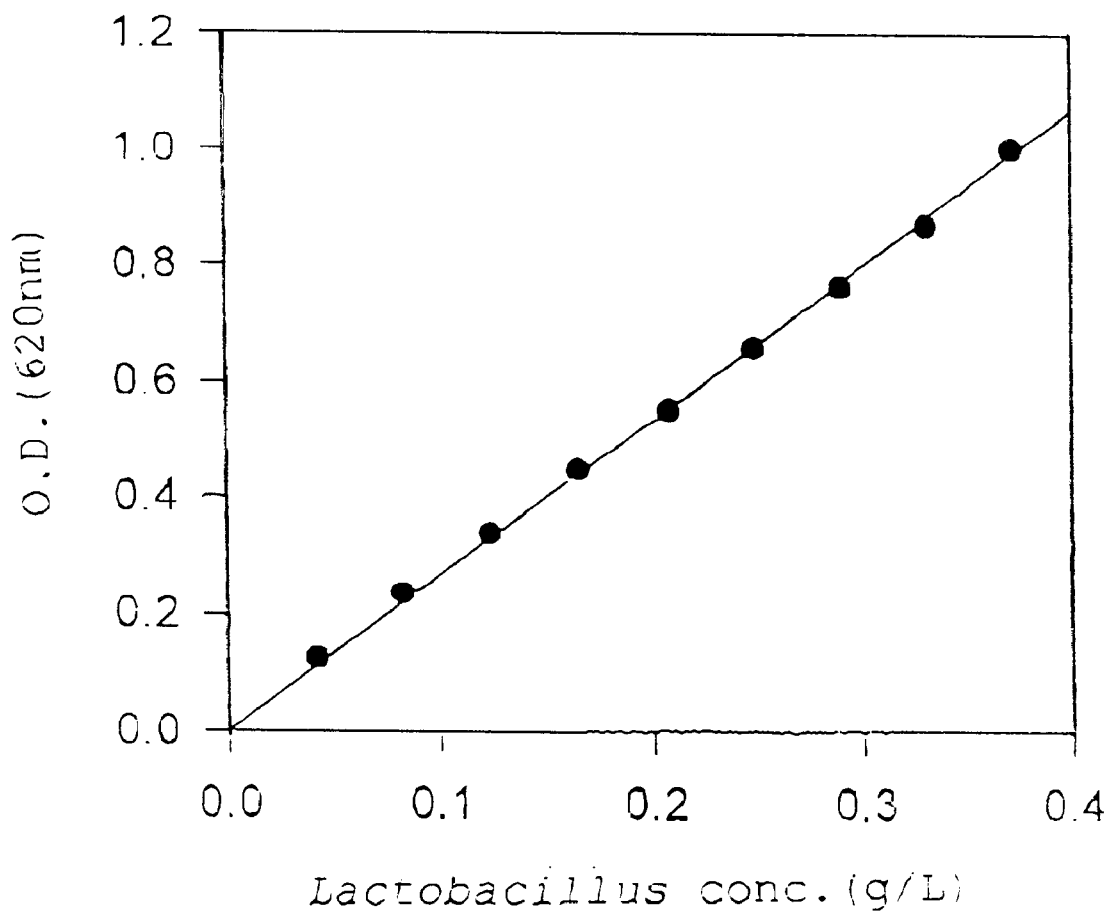
FIG. 6 is a graph showing the relationship between the absorbance measured with a 1 cm-cuvette used in conventional spectrophotometers and Lactobacillus concentration.
Figure 7:
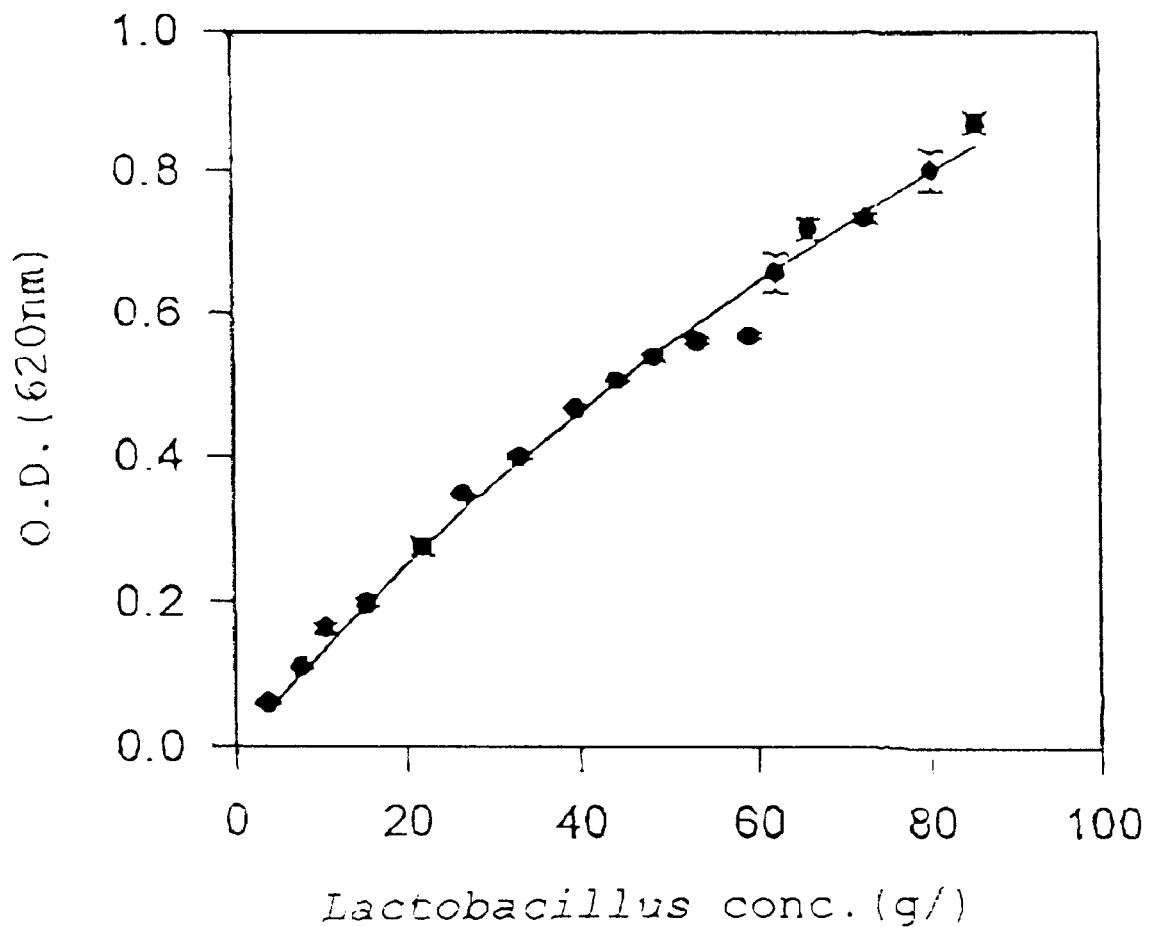
FIG. 7 is a graph showing the relationship between the absorbance measured by a spectrophotometer fitted with the sealed high-density on-line measuring device and Lactobacillus concentration which is calculated by a saturation-type equation.

FIG. 6 shows the relationship between Lactobacillus concentration and the absorbance measured by a conventional spectrophotometer with a 1 cm-cuvette at the wavelength of 620 nm. As show in FIG. 6, the cell concentration shows linearity for the absorbance to the level of about 0.4 g/L. FIG. 7 represents the relationship between Lactobacillus concentration and the absorbance measured by the sealed high-density on-line measuring device of the invention, according to the saturation-type equation shown in Example 1 where constants a and b for Lactobacillus are 214.3 and 2.93, respectively. Measuring absorbance with the sealed high-density on-line measuring device was performed, while maintaining 47 $\mu$m of effective path length of radiated light regulated with a micrometer. As shown in FIG. 7, linearity between the absorbance and the Lactobacillus concentration revealed to the concentration of about 40 g/L, which confirms that the sealed high-density on-line measuring device of the invention can extend the linearity region by more than 100 times than that of conventional measurement.

EXAMPLE 3

Determination of the absorbance of levan containing solution

The absorbance of levan containing solution was measured by the aid of sealed on-line measuring device of the invention. A spectrophotometer (HP-8453, Hewlett-Packard, U.S.A.) was first fitted with the sealed on-line measuring device, and the beaker containing the solution of levan, a water-soluble polysaccharide polymer whose monomer is β-D-fructose, was connected with the sealed high-density on-line measuring device. Then, the levan containing solution was circulated into of the spectrophotometer using a pump, and the absorbance was measured using 400 nm radiant light in a repetitive manner, while changing the concentration of the levan solution.

Figure 8:
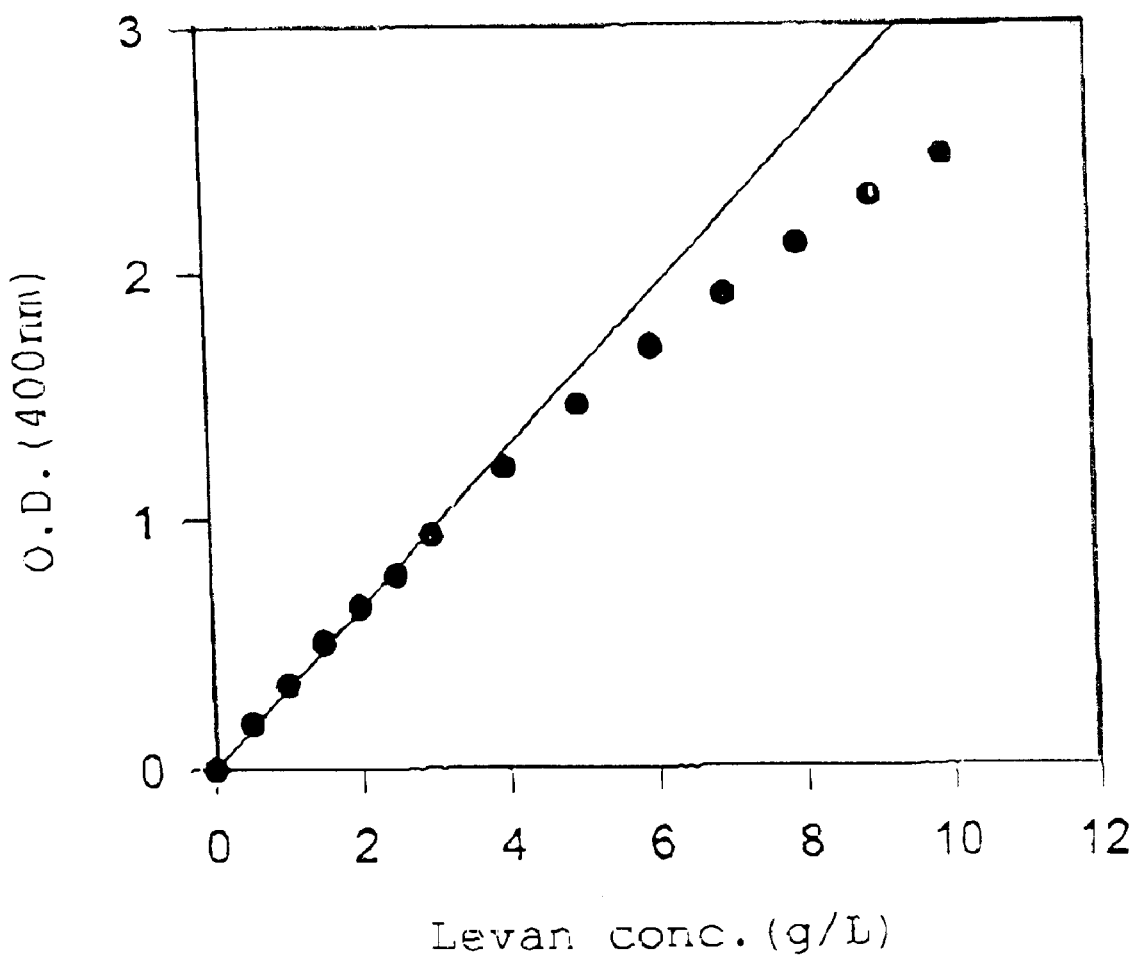
FIG. 8 is a graph showing the relationship between the absorbance of levan containing solution measured with a 1 cm-cuvette used in conventional spectrophotometers and the concentration of levan containing solution.
Figure 9:
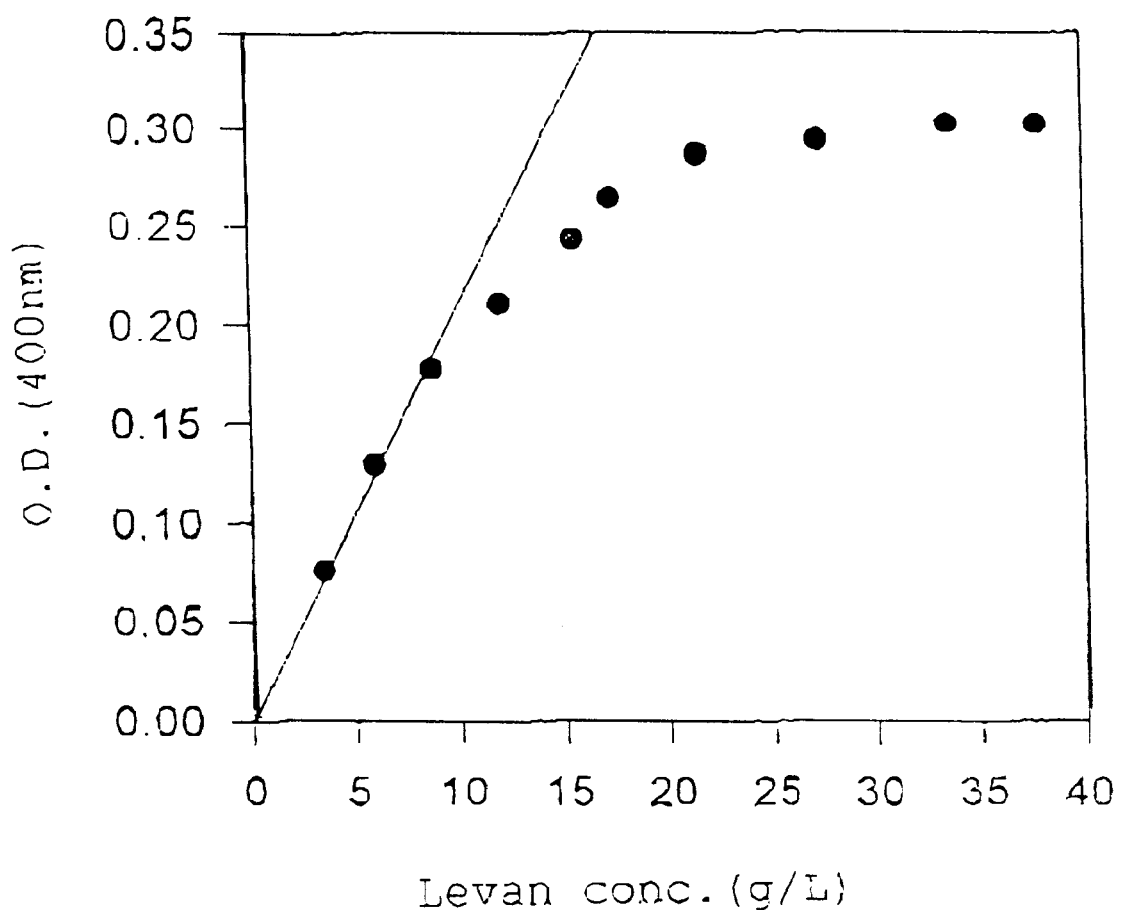
FIG. 9 is a graph showing the relationship between the absorbance and the concentration of levan containing solution, when light path length of a spectrophotometer fitted with the sealed high-density on-line measuring device is 650 $\mu$m.

FIGS. 8 and 9 show the absorbance changes of levan solution measured by a 1-cm cuvette of conventional spectrophotometer and the sealed high-density on-line measuring device where the path length of effective radiant light was 650 $\mu$m. As shown in FIGS. 8 and 9, it was clearly determined that: the sealed high-density on-line measuring device extends the linearity region by about 9 times than that of conventional method, which guarantees the reliable measurement of high concentration of dissolved materials in solutions as well as fermented microorganisms.

EXAMPLE 4

Determination of the absorbance of bovine serum albumin containing solution

Figure 10:
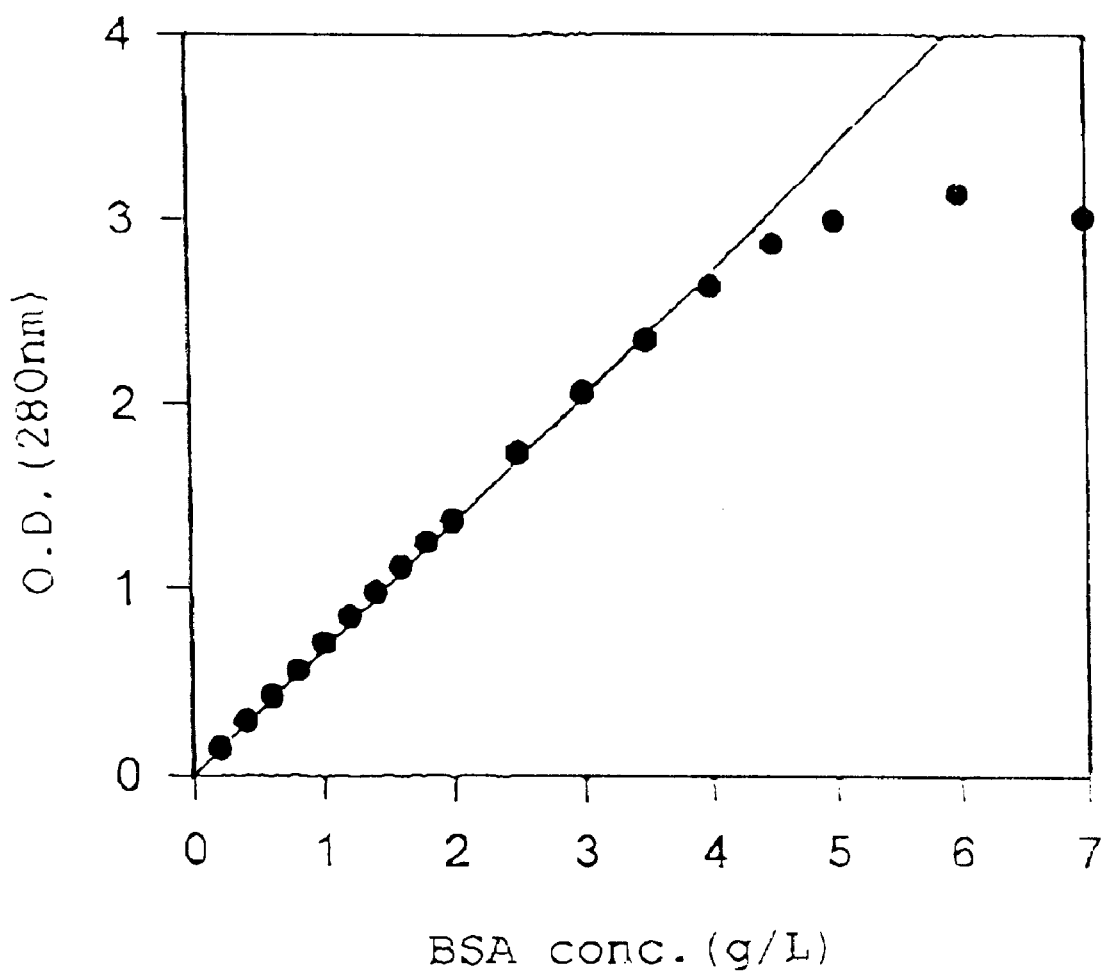
FIG. 10 is a graph showing the relationship between the absorbance of a bovine serum albumin(BSA) containing solution measured with a 1 cm-cuvette used in conventional spectrophotometers and the BSA concentration.
Figure 11:
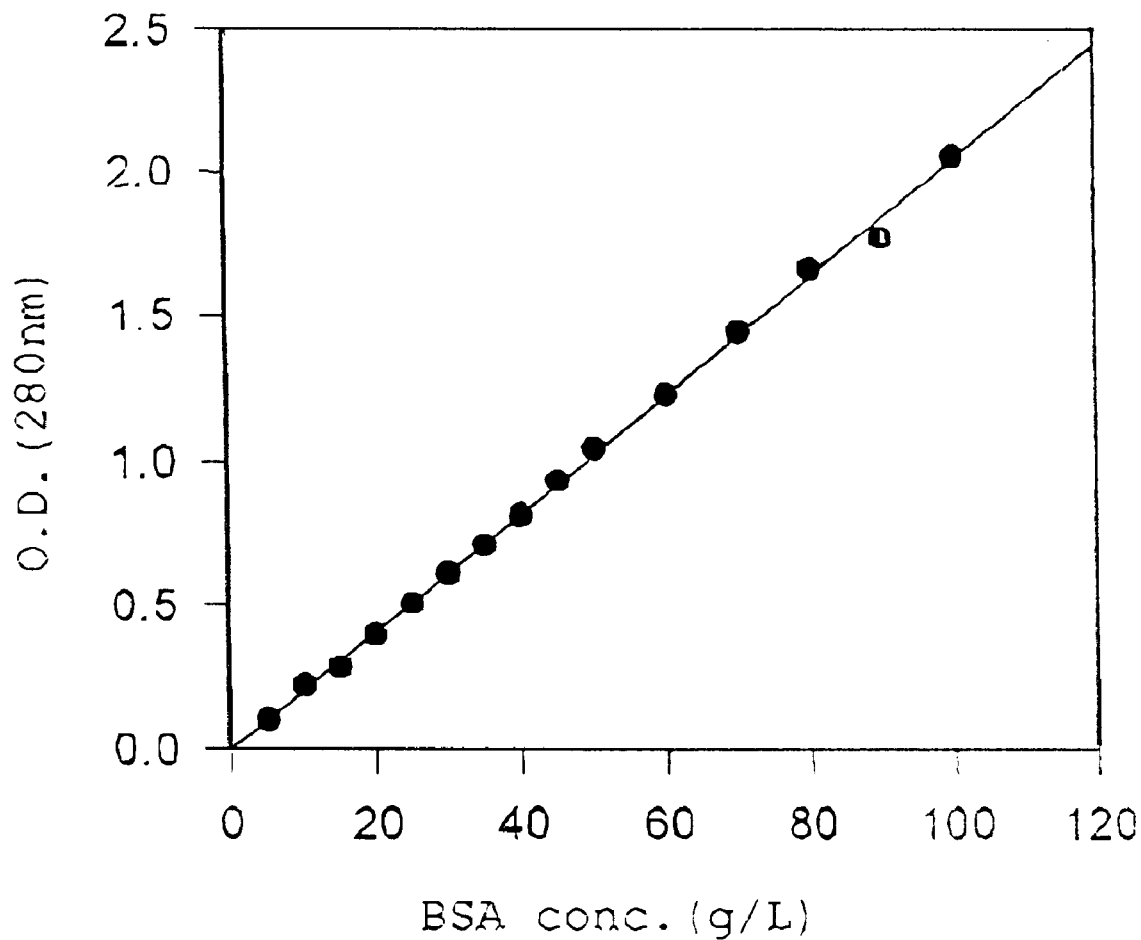
FIG. 11 is a graph showing the relationship between the absorbance and the concentration of a bovine serum albumin containing solution, when light path length of a spectrophotometer fitted with the sealed high-density on-line measuring device is 300 $\mu$m.

To investigate the absorbance changes depending on albumin concentration, the absorbance was measured using a radiant light of 280 nm by a spectrophotometer (HP-8453, Hewlett-Packard, U.S.A.) with a 1 cm-cuvette used in conventional spectrophotometers(see: FIG. 10). Then, a beaker containing albumin solution was connected with a sealed high-density on-line measuring device of the invention, and the absorbance was measured using a radiant light of 280 nm while circulating the aqueous solution into the inside of the device using a pump(see: FIG. 11). At this moment, the transmission length of the effective radiant light was 650 $\mu$m. FIG. 11 confirms that BSA concentration can be measured to the level of about 100 g/L and the sealed high-density on-line measuring device can be applied in determining concentrations of the dissolved materials in solutions.

EXAMPLE 5

Figure 12:
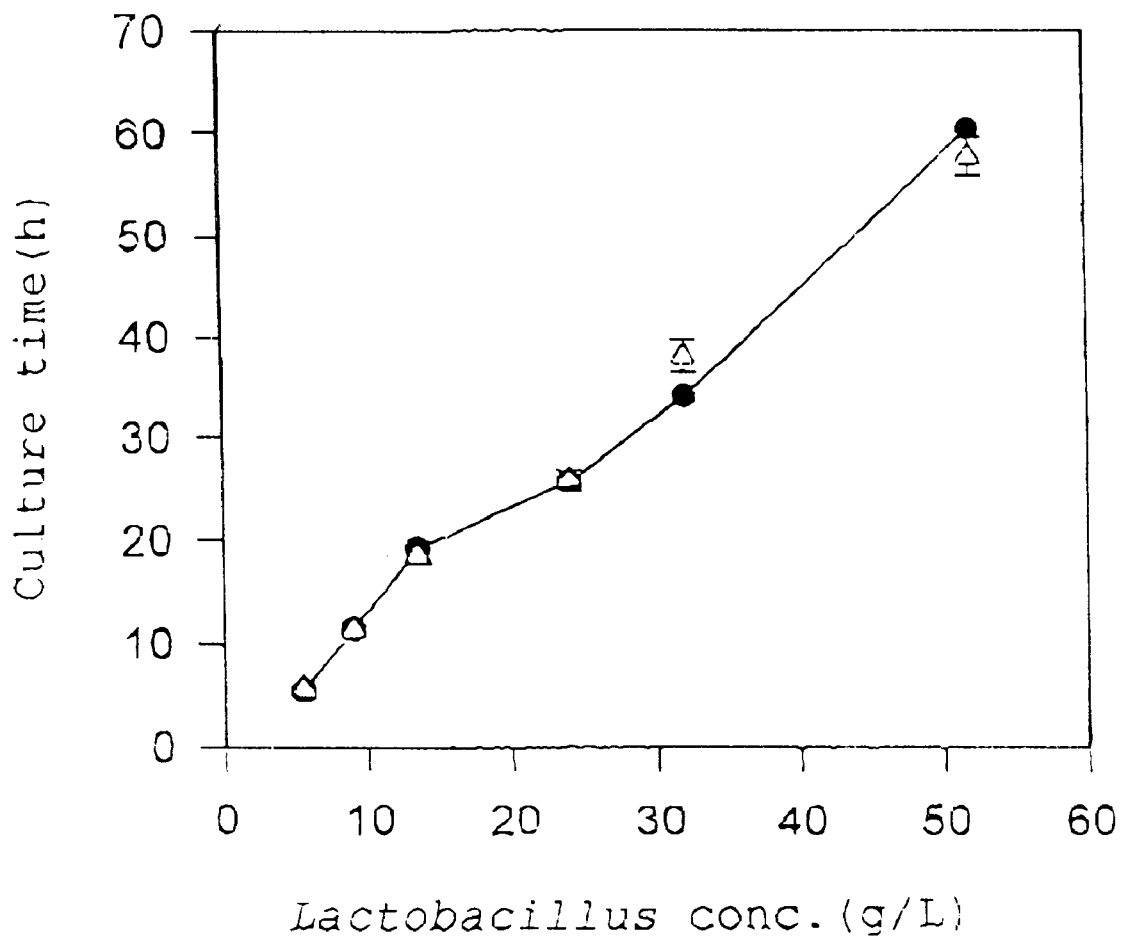
FIG. 12 is a graph of comparing the concentration of Lactobacillus calculated from the absorbance measured by a spectrophotometer fitted with the sealed high-density on-line measuring device and a standard curve with the actual cell concentration measured by dry weight method.

On-line measuring of the cell concentration in a reactor of Lactobacillus fermination Using a ultrafiltration membrane, high-density Lactobacillus was continuously cultured as follows: First, to a 5-liter fermenter(Korea fermenter Inc., Korea) was added initial volume of 2 L medium, and the medium was supplied continuously using a pump at a velocity of 1.1 ml/min for the first 20 hours and 3.5 ml/min for later on. The composition of medium, culturing temperature, pH, shaking speed, and aeration rate were the same as in Example 2. The medium in a fermenter passed through the ultrafiltration membrane by a pump and was circulated into the reactor. Total cell recycle was employed to concentrate cells, where the medium is permeable to the ultrafiltration membrane and the microorganisms is impermeable to the membrane to be returned to the reactor, which made the cell concentration of up to 60 g/L in 52 hours. In continuous culture of high-density Lactobacillus using the ultrafiltration membrane as described above, time course of cell concentration changes in a fermenter was observed using the on-line measuring device of the invention, where wavelength of radiated light was 620 nm and the effective path length was 47 $\mu$m. The cell concentrations calculated from the absorbance measured by the on-line measuring device and the standard curve showing the relationship between the absorbance and cell concentration were almost the same as the actual cell concentration measured by dry weight method(see: Table 3, FIG. 12). The results confirmed that the device can be applicable to the continuous measurement of cell concentration in a fermentor. In FIG. 12, the error ranges shown in graph represent the mean deviations of five times of measuring cell concentrations by the sealed on-line measuring device, where the actual cell concentrations and measured values by the sealed on-line measuring device were represented as (-●-) and (-Δ-), respectively.

TABLE 3

The actual cell concentrations of Lactobacillus, the measured values by the sealed on-line measuring device of the invention and error ranges thereof

| Actual cell concentration (g/L) | 5.50 | 11.42 | 19.14 | 25.8 | 34.22 | 80.52 |
|---|---|---|---|---|---|---|
| Measured value (g/L, mean) | 5.81 | 11.41 | 18.57 | 26.01 | 38.20 | 57.84 |
| Error (%) | −5.64 | 0.09 | 2.90 | −0.91 | −11.63 | 4.43 |

As clearly illustrated and explained as above, the present invention provides a novel sealed on-line measuring device which is able to regulate path length of the radiated light in solution. In accordance with the sealed on-line measuring device, high concentrations of samples in solutions can be measured without dilution, by way of employing a newly designed cuvette holder in a spectrophotometer fitted to a reactor.

What is claimed is:

1. A sealed high-density on-line measuring device for use in a spectrophotometer whose cuvette holder is linked to a reactor, which comprises:
    a base;
    a fixed plate adapted for light passage, which is vertically placed on the base;
    a moving plate adapted for light radiation, which is vertically placed on the base at an opposite side to the fixed plate so that it can slide on the base horizontally;
    an inlet and an outlet for sample passage, each of which is positioned at the outer side of the moving plate and communicating with a space between the fixed and moving plates;
    a metal ring linking the fixed plate and the moving plate; and,
    upper and lower shielders each of whose ends is in contact with the fixed plate and moving plate, respectively, to give a sealed space.

2. The sealed high-density on-line measuring device of claim 1, wherein the path length of the radiated light is regulated by fine control of a distance between the fixed plate and the moving plate.

3. The sealed high-density on-line measuring device of claim 1, wherein each of the fixed plate and the moving plate has a round-shaped hole at the same position to pass the radiated light through them.

4. The sealed high-density on-line measuring device of claim 1, wherein each of the fixed plate and the moving plate has a transparent plate attached on its sealed space-faced side.

5. The sealed high-density on-line measuring device of claim 1, wherein the metal ring comprises a sliding bearing.

6. The sealed high-density on-line measuring device of claim 1, wherein the shielder is made of pleated flexible material or elastic material.

7. The sealed high-density on-line measuring device of claim 1, wherein the shielder is a metal ring covered with rubber.

8. The sealed high-density on-line measuring device of claim 1, which further comprises a micrometer for fine control of sliding movement of the moving plate.

9. The sealed high-density on-line measuring device of claim 1, which further comprises a spring wiring a metal ring which is positioned between the fixed plate and moving plate to convey minor rotation of the micrometer to the moving plate.

* * * * *